US00PP17622P2

(12) United States Plant Patent
Santoyo

(10) Patent No.: US PP17,622 P2
(45) Date of Patent: Apr. 17, 2007

(54) JUNIPER PLANT NAMED 'MONSAN'

(50) Latin Name: *Juniperus×pfitzeriana*
Varietal Denomination: Monsan

(75) Inventor: Jose Santoyo, Visalia, CA (US)

(73) Assignee: Monrovia Growers, Azusa, CA (US)

( * ) Notice: Subject to any disclaimer, the term of this patent is extended or adjusted under 35 U.S.C. 154(b) by 0 days.

(21) Appl. No.: 11/248,759

(22) Filed: Oct. 12, 2005

(51) Int. Cl.
*A01H 5/00* (2006.01)

(52) U.S. Cl. ..... Plt./214

(58) Field of Classification Search ..... Plt./214
See application file for complete search history.

*Primary Examiner*—Kent Bell
(74) *Attorney, Agent, or Firm*—C. A. Whealy

(57) ABSTRACT

A new and distinct cultivar of Juniper plant named 'Monsan', characterized by its compact, low growing, outwardly spreading, recumbent and rounded plant habit; lacy and graceful leaves that are initially yellow and become yellow green in color with development; and tolerance to low temperatures.

1 Drawing Sheet

Botanical designation: *Juniperus×pfitzeriana.*
Cultivar denomination: 'Monsan'.

BACKGROUND OF THE INVENTION

The present Invention relates to a new and distinct cultivar of Juniper plant, botanically known as *Juniperus×pfitzeriana,* and hereinafter referred to by the cultivar name Monsan.

The new Juniper is a naturally-occurring whole plant mutation of the *Juniperus×pfitzeriana* cultivar Aurea Improved, disclosed in U.S. Plant Pat. No. 2,491. The new Juniper was discovered and selected by the Inventor as a single plant within a population of plants of the parent cultivar in Dayton, Oreg. in 1995.

Asexual reproduction of the new cultivar by stem cuttings in a controlled environment in Visalia, Calif., since 1996, has shown that the unique features of this new Juniper are stable and reproduced true to type in successive generations.

SUMMARY OF THE INVENTION

Plants of the cultivar Monsan have not been observed under all possible environmental conditions. The phenotype may vary somewhat with variations in environment and culture such as temperature and light intensity, without however, any variance in genotype.

The following traits have been repeatedly observed and are determined to be the unique characteristics of 'Monsan'. These characteristics in combination distinguish 'Monsan' as a new and distinct Juniper cultivar:

1. Compact, low growing, outwardly spreading, recumbent and rounded plant habit.
2. Lacy and graceful leaves that are initially yellow and become yellow green in color with development.
3. Tolerant to low temperatures; not susceptible to winter tip burn.

Plants of the new Juniper can be compared to plants of the parent, the cultivar Aurea Improved. In side-by-side comparisons conducted in Azusa, Calif., plants of the new Juniper differed from plants of the cultivar Aurea Improved in the following characteristics:

1. Developing leaves of plants of the new Juniper were yellow in color whereas developing leaves of plants of the cultivar Aurea Improved were yellow green in color.
2. Fully expanded leaves of plants of the new Juniper were yellow green in color whereas fully expanded leaves of plants of the cultivar Aurea Improved were light green in color.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the colors of the new Juniper.

The photograph at the bottom of sheet comprises a side perspective view of a typical plant of 'Monsan' grown in a container.

The photographs at the top of the sheet comprise close-up views of typical branches and leaves of 'Monsan'.

DETAILED BOTANICAL DESCRIPTION

In the following description, color references are made to The Royal Horticultural Society Colour Chart, 1995 Edition, except where general terms of ordinary dictionary significance are used. Plants used for the aforementioned photographs and following description were grown in five-gallon containers in an outdoor nursery for about three to four years in Visalia, Calif. During the production of the plants, day temperatures ranged from about 24° C. to about 29° C. and night temperatures ranged from about 4° C. to about 12° C.

Botanical classification: *Juniperus×pfitzeriana* cultivar Monsan.

Parentage: Naturally-occurring whole plant mutation of the *Juniperus×pfitzeriana* cultivar Aurea Improved, disclosed in U.S. Plant Pat. No. 2,491.

Propagation:

*Type cutting.*—Stem cuttings.

*Time to initiate roots.*—About five months.

*Time to produce a rooted young plant.*—About ten months.

*Root description.*—Medium to thick, fibrous; white to beige in color.

*Rooting habit.*—Freely branching.

Plant description:

*Form.*—Perennial evergreen shrub; compact, low growing, outwardly spreading, recumbent and rounded plant habit. Freely branching; about 20 lateral branches per plant.

*Plant height.*—About 16 cm.

*Plant diameter.*—About 56 cm.

*Lateral branches.*—Length: About 28 cm. Diameter: About 6 mm. Internode length: About 1.5 cm. Strength: Strong. Texture: Smooth, glabrous. Color, young: Close to 2C. Color, woody: Close to 200D.

*Foliage description.*—Arrangement: Opposite; simple. Length: About 5 mm. Width: About 1 mm. Shape: Narrow, scale-like. Apex: Acute. Base: Clasping; sessile. Margin: Entire. Texture, upper and lower surfaces: Glabrous; durable. Venation pattern: Parallel. Color: Developing foliage, upper and lower surfaces: Close to 1B. Fully expanded foliage, upper and lower surfaces: Close to 144A; with development, overlain with 189A. Venation, upper and lower surfaces: Similar to lamina. Venation, lower surface: Midrib, close to 185A; lateral veins, close to 148A.

Cone description: Plants of the new Juniper have not been observed to produce cones.

Disease/pest resistance: Plants of the new Juniper grown in the garden have not been noted to be resistant to pathogens and pests common to Juniper.

Weather tolerance: Plants of the new Juniper have been observed to be very tolerant to rain and wind.

Temperature tolerance: Plants of the new Juniper have been observed to be tolerant to temperatures ranging from about −20° C. to 43° C. Plants of the new Juniper are not susceptible to winter tip burn.

It is claimed:

1. A new and distinct cultivar of Juniper plant named 'Monsan', as illustrated and described.

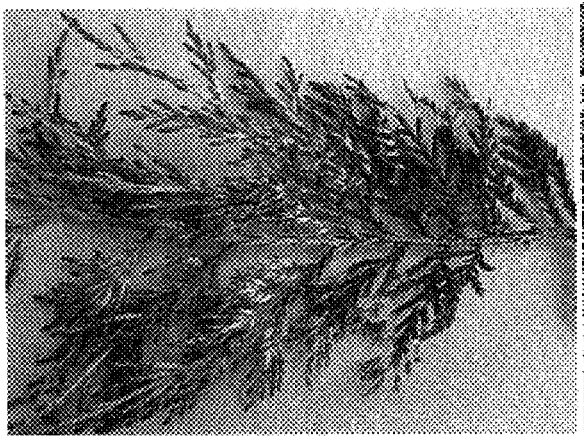
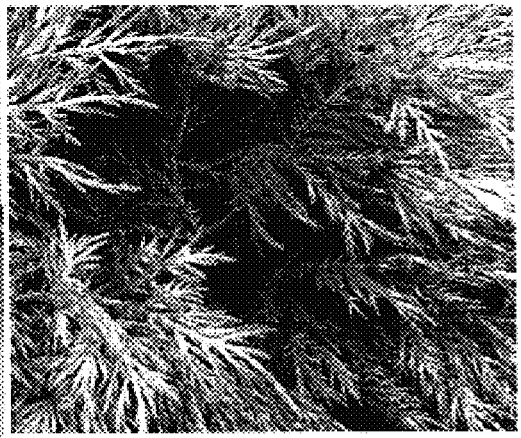
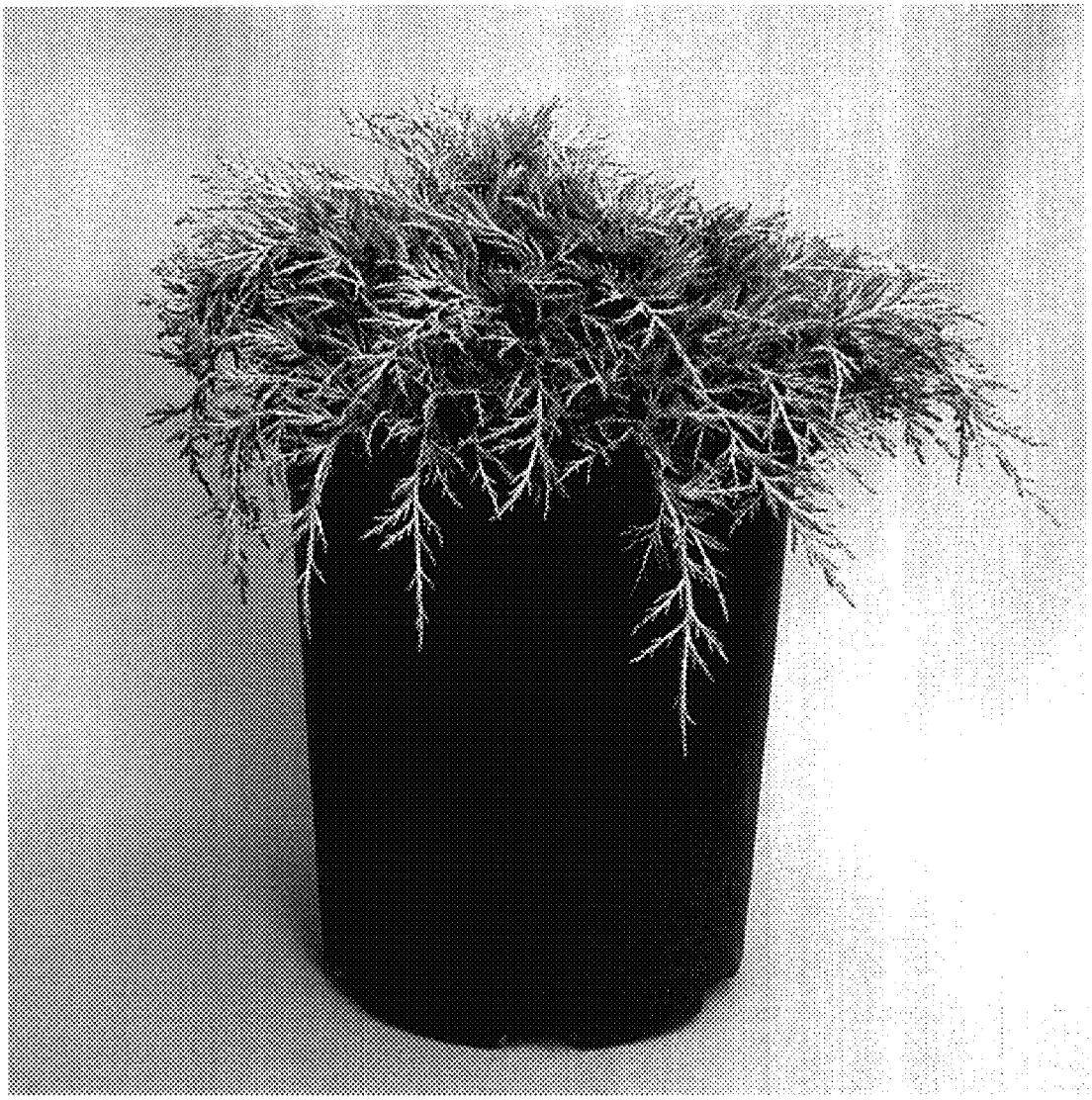

* * * * *